(12) United States Patent
Hall et al.

(10) Patent No.: US 11,740,119 B2
(45) Date of Patent: Aug. 29, 2023

(54) TOILET WITH FLOATING SEAT FOR WEIGHT MEASUREMENT

(71) Applicant: Medic, Inc., Provo, UT (US)

(72) Inventors: David R. Hall, Provo, UT (US); Joshua Larsen, Provo, UT (US); Jared Blake, Provo, UT (US); Jared Reynolds, Provo, UT (US)

(73) Assignee: Hall Labs LLC, Provo, UT (US)

( * ) Notice: Subject to any disclaimer, the term of this patent is extended or adjusted under 35 U.S.C. 154(b) by 0 days.

(21) Appl. No.: 16/884,872

(22) Filed: May 27, 2020

(65) Prior Publication Data

US 2020/0393288 A1 Dec. 17, 2020

Related U.S. Application Data

(63) Continuation-in-part of application No. 16/828,000, filed on Mar. 24, 2020, now abandoned.

(60) Provisional application No. 62/907,408, filed on Oct. 9, 2019, provisional application No. 62/907,432, filed on Sep. 27, 2019, provisional application No. 62/892,927, filed on Aug. 28, 2019, provisional application No. 62/888,683, filed on Aug. 19, 2019, provisional application No. 62/862,547, filed on Jun. 17, 2019, provisional application No. 62/862,564, filed on Jun. 17, 2019.

(51) Int. Cl.
| | |
|---|---|
| *G01G 19/50* | (2006.01) |
| *G01N 33/483* | (2006.01) |
| *A47K 13/12* | (2006.01) |
| *G01G 19/52* | (2006.01) |

(52) U.S. Cl.
CPC ............. *G01G 19/50* (2013.01); *A47K 13/12* (2013.01); *G01G 19/52* (2013.01); *G01N 33/4833* (2013.01)

(58) Field of Classification Search
CPC ........ A47K 13/12; A47K 13/24; G01G 19/50; G01G 19/52
See application file for complete search history.

(56) References Cited

U.S. PATENT DOCUMENTS

| | | | | |
|---|---|---|---|---|
| 2,693,602 | A * | 11/1954 | Campbell | A47K 13/06 16/268 |
| 4,314,382 | A * | 2/1982 | Ginsburg | A47K 13/12 4/236 |
| 4,697,656 | A * | 10/1987 | de Canecaude | G01G 19/44 177/144 |
| 7,437,781 | B2 * | 10/2008 | Rigas | A47K 13/24 4/661 |
| 11,141,030 | B2 * | 10/2021 | Newham | A47K 13/24 |
| 2016/0000378 | A1 * | 1/2016 | Hall | A61B 5/14532 702/19 |
| 2016/0374619 | A1 * | 12/2016 | Borkholder | A61B 5/1102 600/301 |
| 2018/0031411 | A1 * | 2/2018 | Hall | G01G 21/23 |

* cited by examiner

*Primary Examiner* — Erin Deery (57) ABSTRACT

An analytical toilet comprising a frame supporting a bowl for receiving excreta; a floating seat for a user to sit above the bowl; one or more seat load cells for measuring weight on the seat; and a floating hinge connecting the floating seat to the frame is disclosed. The floating hinge may comprise a pivot bar rotatably connected to both the toilet seat and the toilet body.

16 Claims, 11 Drawing Sheets

TOILET WITH FLOATING SEAT FOR WEIGHT MEASUREMENT

CROSS-REFERENCE TO RELATED APPLICATIONS

This application is a continuation-in-part of U.S. patent application Ser. No. 16/828,000 titled "Toilet with Floating Bowl for Weighing Excreta" filed on 24 Mar. 2020 which claims priority to U.S. Provisional Patent Application Nos. 62/862,564 titled "Toilet with Frame, Bowl and Shroud" filed on Jun. 17, 2019; 62/888,683 titled "Toilet with Multiple Point Lifting System" filed Aug. 19, 2019; 62/892,927 filed on Aug. 28, 2019; 62/907,408 titled "Toilet with Personalized Lifting System for Bowl and Seat" filed on Oct. 9, 2019; and 62/907,432 titled "Toilet with User Weight Driven Seat Lift Profile" filed on Sep. 27, 2019; each of which are incorporated herein by reference in their entireties. This application also claims priority to U.S. Provisional Patent Application No. 62/862,547 titled "Toilet with Floating Seat for Weight Measurement" filed on 17 Jun. 2019, which is incorporated herein by reference in its entirety.

TECHNICAL FIELD

The present disclosure relates to analytical toilets. More particularly, it relates to analytical medical toilets equipped to provide health and wellness information to the user.

BACKGROUND

The ability to track an individual's health and wellness is currently limited due to the lack of available data related to personal health. Many diagnostic tools are based on examination and testing of excreta, but the high cost of frequent doctor's visits and/or scans make these options available only on a very limited and infrequent basis. Thus, they are not widely available to people interested in tracking their own personal wellbeing.

Toilets present a fertile environment for locating a variety of useful sensors to detect, analyze, and track trends for multiple health conditions. Locating sensors in such a location allows for passive observation and tracking on a regular basis of daily visits without the necessity of visiting a medical clinic for collection of samples and data. Monitoring trends over time of health conditions supports continual wellness monitoring and maintenance rather than waiting for symptoms to appear and become severe enough to motivate a person to seek care. At that point, preventative care may be eliminated as an option leaving only more intrusive and potentially less effective curative treatments. An ounce of prevention is worth a pound of cure.

A toilet seat and lid have ample surface area in direct contact with body parts (thighs and/or back, etc.). This direct contact can be suitable locations for sensor placement. Therefore, it is highly advantageous to be able to upgrade a toilet seat or a toilet lid with newer versions that provide additional capabilities. Conventional toilet designs firmly attached the toilet seat and lid to the toilet itself. New toilet designs that enable health and wellness monitoring need to allow replacing an existing toilet seat and/or lid to be replaced as more advanced seat or lid designs become available.

Just a few examples of smart toilets and other bathroom devices can be seen in the following U.S. Patents and Published Applications: U.S. Pat. No. 9,867,513, entitled "Medical Toilet With User Authentication"; U.S. Pat. No. 10,123,784, entitled "In Situ Specimen Collection Receptacle In A Toilet And Being In Communication With A Spectral Analyzer"; U.S. Pat. No. 10,273,674, entitled "Toilet Bowl For Separating Fecal Matter And Urine For Collection And Analysis"; US 2016/0000378, entitled "Human Health Property Monitoring System"; US 2018/0020984, entitled "Method Of Monitoring Health While Using A Toilet"; US 2018/0055488, entitled "Toilet Volatile Organic Compound Analysis System For Urine"; US 2018/0078191, entitled "Medical Toilet For Collecting And Analyzing Multiple Metrics"; US 2018/0140284, entitled "Medical Toilet With User Customized Health Metric Validation System"; US 2018/0165417, entitled "Bathroom Telemedicine Station." The disclosures of all these patents and applications are incorporated by reference in their entireties.

SUMMARY

In a first aspect, the disclosure provides an analytical toilet comprising a frame supporting a bowl for receiving excreta; a floating seat for a user to sit above the bowl; one or more seat load cells for measuring weight on the seat; and a floating hinge connecting the floating seat to the frame.

Further aspects and embodiments are provided in the foregoing drawings, detailed description and claims.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, "toilet" is meant to refer to any device or system for receiving human excreta, including urinals.

As used herein, the term "bowl" refers to the portion of a toilet that is designed to receive excreta.

As used herein, the term "base" refers to the portion of the toilet below and around the bowl supporting it.

As used herein, the term "user" refers to any individual who interacts with the toilet and deposits excreta therein.

As used herein, the term "excreta" refers to any substance released from the body of a user including urine, feces, menstrual discharge, saliva, expectorate, and anything contained or excreted therewith.

As used herein, the term "sensor" is meant to refer to any device for detecting and/or measuring a property of a person or of a substance regardless of how that property is detected or measured, including the absence of a target molecule or characteristic. Sensors may use a variety of technologies including, but not limited to, MOS (metal oxide semiconductor), CMOS (complementary metal oxide semiconductor), CCD (charge-coupled device), FET (field-effect transistors), nano-FET, MOSFET (metal oxide semiconductor field-effect transistors), load cells, weight sensors, spectrometers, volume measurement devices, durometers, temperature gauges, chromatographs, mass spectrometers, IR (infrared) detector, near IR detector, visible light detectors, and electrodes, microphones, pressure gauges, rheometers, pH detectors, PPG (photoplethysmogram), thermometers (including IR and thermocouples), scent detectors gas, and analyzers.

As used herein, the term "imaging sensor" is meant to refer to any device for detecting and/or measuring a property of a person or of a substance that relies on electromagnetic radiation of any wavelength (e.g., visible light, infrared light, x-ray) or sound waves (e.g., ultrasound) to view the surface or interior of a user or substance. The term "imaging sensor" does not require that an image or picture is created or stored even if the sensor is capable of creating an image.

As used herein, the term "data connection" and similar terms are meant to refer to any wired or wireless means of transmitting analog or digital data and a data connection may refer to a connection within a toilet system or with devices outside the toilet.

As used herein, the term "floating" refers to a component that is supported by weight sensors independently of other components and does not support other components (e.g., a floating bowl does not support the weight of the seat).

As used herein, the term "floating hinge" refers to a hinge that enables rotation while allowing the connecting pieces (e.g., a seat and toilet body) to move relative to each other at least vertically.

As used herein, the term "excretion profile" is meant to refer collectively to the rate of excretion at any moment in time of an excretion event and the total volume or mass of excreta as a function of time during an excretion event. The terms "defecation profile" and "urination profile" refer more specifically to the separate measurement of excreta from the anus and urethra, respectively.

Exemplary Embodiments

The present disclosure relates to analytical toilets designed to acquire health and wellness data about users. More particularly, it relates to an analytical toilet that measures the weight of users. It may also include a variety of other health and wellness sensors to track other health indicators. It also transmits user health and wellness data to other devices so that the data from individual users may be tracked over time.

Figure 1:
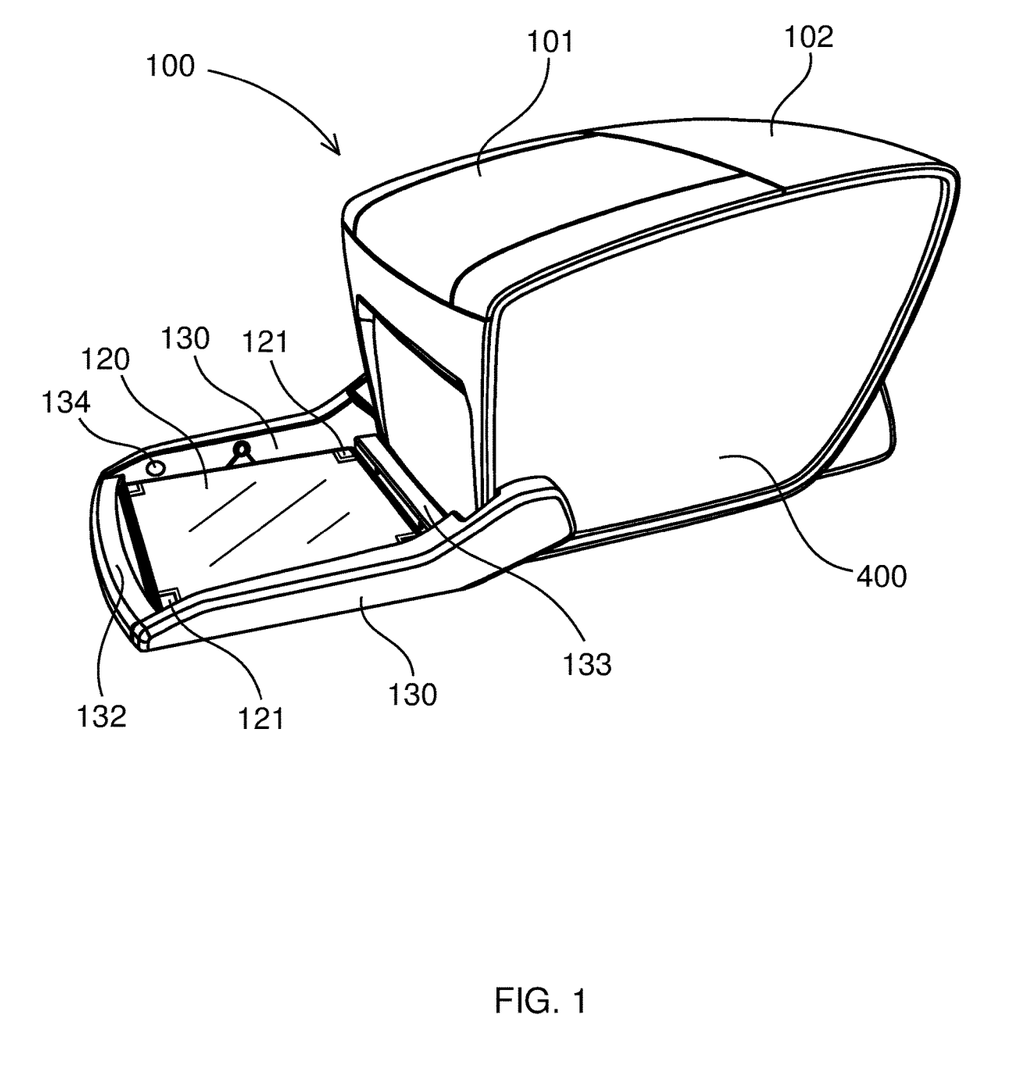
FIG. 1 is a perspective view of a first exemplary toilet according to the present disclosure in a closed position.
Figure 2:
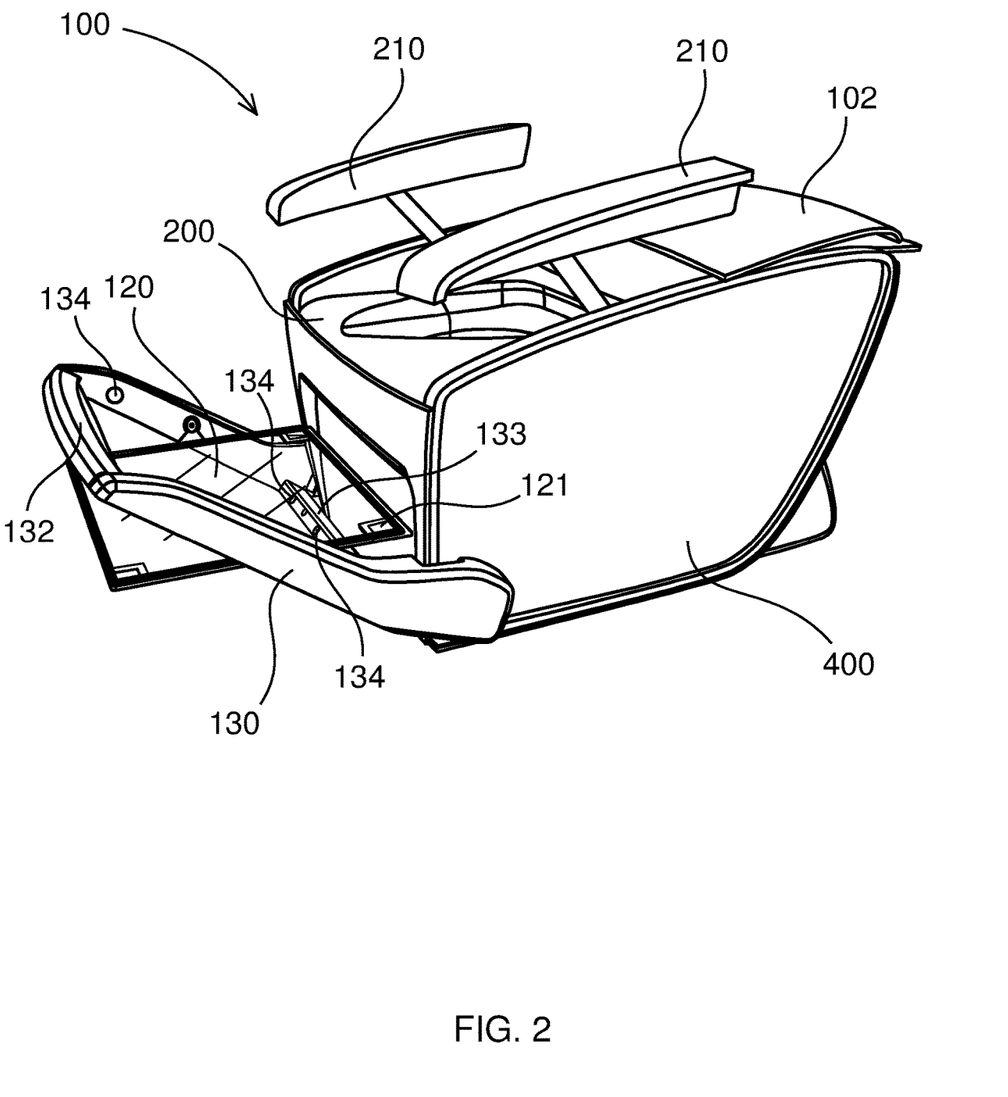
FIG. 2 is a perspective view of the toilet of FIG. 1 with the lid opened and an exemplary embodiment of handles deployed.

Referring to FIG. 1, an exemplary embodiment of a toilet is shown with a closed lid 101, lowered foot platform 120, and retracted handles 210. FIG. 2 shows the toilet with an open lid 101, raised foot platform 120, and extended handles 210. In a preferred embodiment, handles 210 are adapted to be readily ripped by a user, especially while sitting or rising. In a preferred embodiment, the handles 210 move while the seat 200 is lowering and lifting a user to enable them to grip the handles 210 and use them for support during sitting and rising. The toilet is enclosed with a shroud 400.

In various exemplary embodiments, the shroud 400 covers all the internal support components that comprise the frame as well as the bowl 300 (i.e., the bowl is covered except for the top that would be covered by a lid). In preferred embodiments, the shroud 400 comprises at least one sections of articulated or flexible (e.g., elastic, material) assembled such that the shroud 400 can contract or expand as the frame 110 moves the bowl 300 and/or seat 200. Other sections of the shroud may be rigid. In various exemplary embodiments, the at least some portions of the shroud are removable or openable to allow access to the interior of the toilet frame. The interior of the toilet frame may include, among other things, plumbing connections, fluid supply lines, support structures, health and wellness assessment devices, electronic circuits, digital devices (e.g., processors, memory), storage tanks, and communication modules. In various preferred embodiments, cover 102 opens to allow access to the interior of the frame.

In various exemplary embodiments, the shrouds 400 are preferably designed for aesthetic and other purposes. For example, the shrouds 400 can be made in various colors to suit the décor of the bathroom the toilet is installed in. Besides colors, the shrouds 400 can include patterns or graphics so that the toilet 100 "makes a statement" in the bathroom.

In various exemplary embodiments, the handles 210 include at least one buttons, switches, sensors, etc. through which the user may control the seat, including, but not limited to, starting and stopping the seat 200, reversing seat movement direction, adjusting the position or angle of the seat 200, and adjusting the height of the bowl 300, seat 200, or foot platform 120.

In various exemplary embodiments, the handles 210 may include at least one health and wellness sensors. The sensors may be used to measure how hard the user is gripping and provide feedback to the lift control. For example, if a user suddenly increases their grip it is likely that they are struggling with standing or with their balance. Grip pressure may also be tracked over time. The sensors may also include detection for heart rate, body temperature, hand health indicators, light sensors, electrocardiogram, pulse, blood test (e.g., using a finger prick), etc. Toilet handles with health and wellness sensors are disclosed in U.S. Patent Pub. No. 2018/0084959, the entire disclosure of which is incorporated herein by reference in its entirety.

Figure 3:
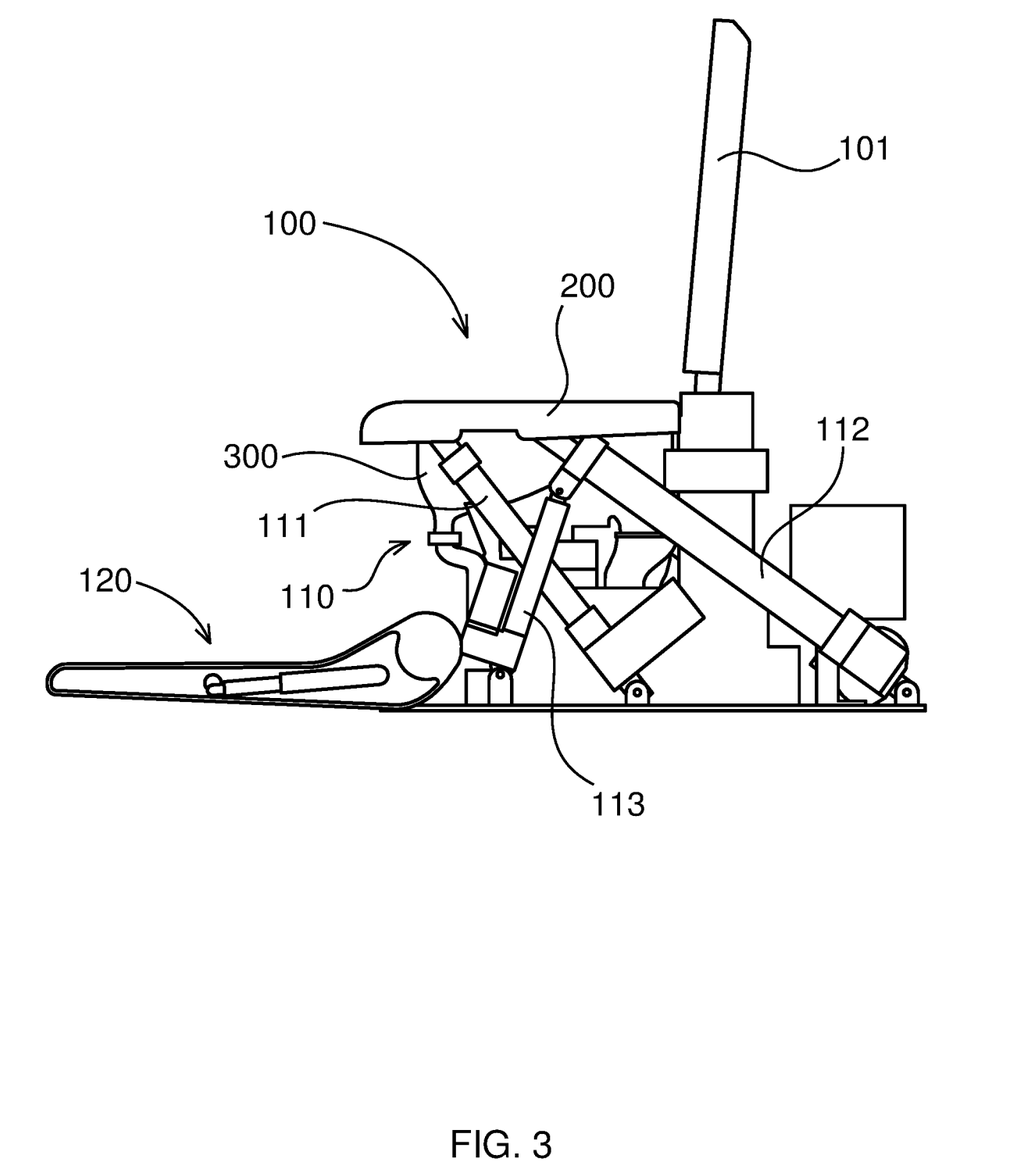
FIG. 3 is a side plan view of a second exemplary toilet according to the present disclosure with the shroud removed and the seat in a lowered position for sitting.

Referring to FIG. 3, an exemplary embodiment of a toilet 100 is shown with various seat elevations. The toilet 100 includes a frame 110, bowl 300 supported by the frame 110, a lid 101, and a seat 200 also supported by the frame 110. In a preferred embodiment, the seat 200 is supported by two sets of seat actuators 111, 112, and 113. In other embodiments, the number and arrangement of actuators may vary.

In a preferred embodiment, a pair of first seat actuators 111 are pivotally connected to a front area of the seat 200 and a pair of second seat actuators 112 are pivotally connected to a back area of the seat 200 providing support at four "corners" of the seat 200. The four seat actuators 111 and 112 are also pivotally attached to the frame 110. An additional pair of third seat actuators 113 are pivotally attached to the frame 110 at one end and pivotally attached to the second pair of seat actuators 112 at their other end. In another embodiment, the third seat actuators 113 are attached to the first pair of seat actuators 111.

Figure 4:
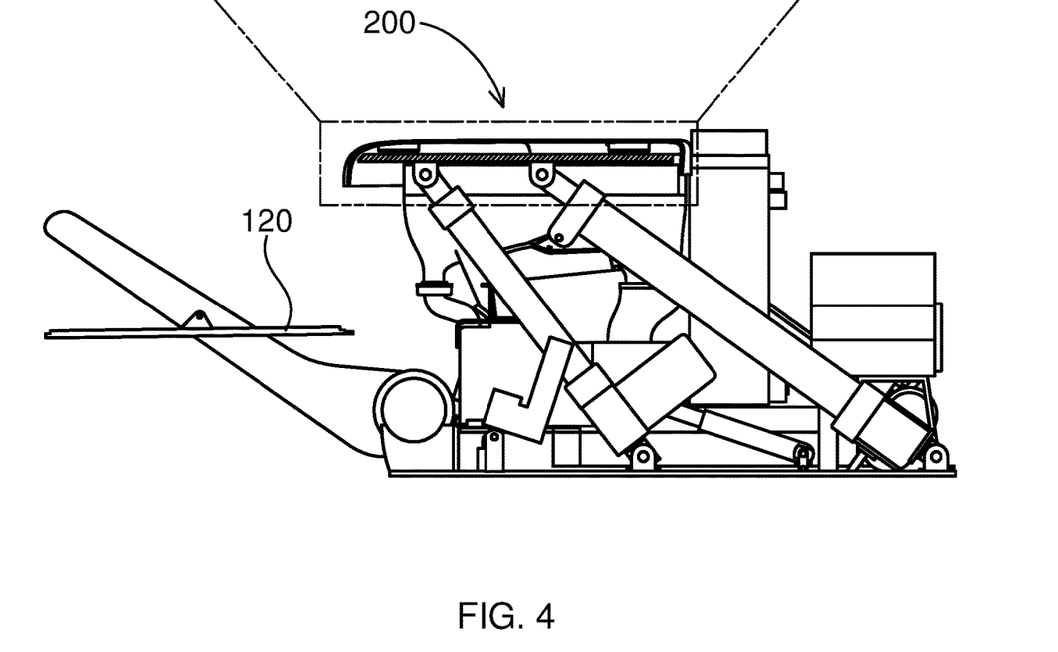
FIG. 4 is a side cross-sectional view of the toilet of FIG. 1.
Figure 4A:
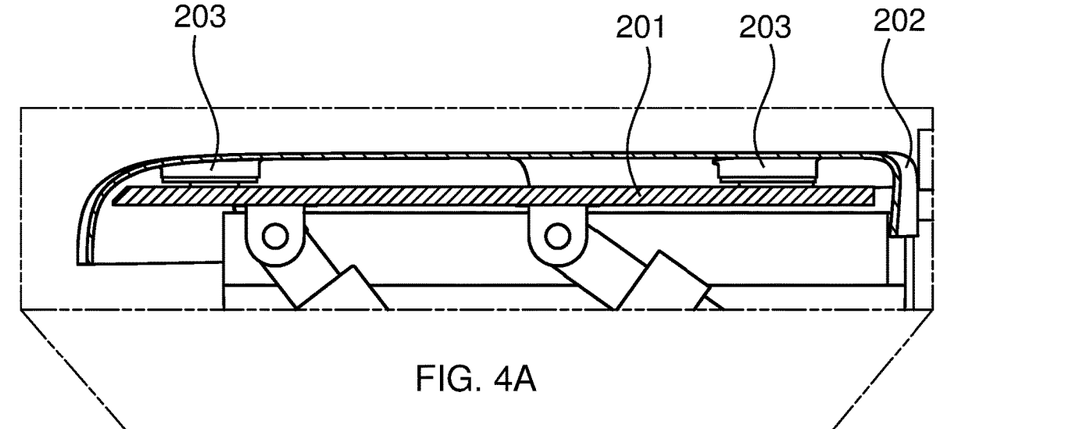
FIG. 4A is close-up view of the seat as shown in FIG. 4.

Referring to FIGS. 4 and 4A, an exemplary embodiment of a floating toilet seat 200 according to the present disclosure is shown. The seat includes a rigid seat support 201 covered by a shroud 202. Weight sensors 203 are placed between the seat support 201 and floating cover 202. In various other embodiments, the weight sensors may be placed in a variety of places such as under the actuators or under the frame.

In various exemplary embodiments, the toilet continuously measures weight load on both the seat 200 and the foot platform 120. In a preferred embodiment, the system weighs the user on the foot platform 120 prior to the user placing any weight against the seat 200 and records that as the user's total weight. In some embodiments, the system calculates a user total weight using both the seat weight sensors 203 and foot platform weight sensors 121 after the user seated with the seat 200 fully lowered. In various exemplary embodiments, the system calculates the percentage of user body weight on the foot platform 120. The angle of the seat 200 is limited from raising based on the percentage of weight on the foot platform 120. This prevents the seat 200 from tipping to an angle that will not support the user's weight prior to the user being on their feet.

Figure 5:
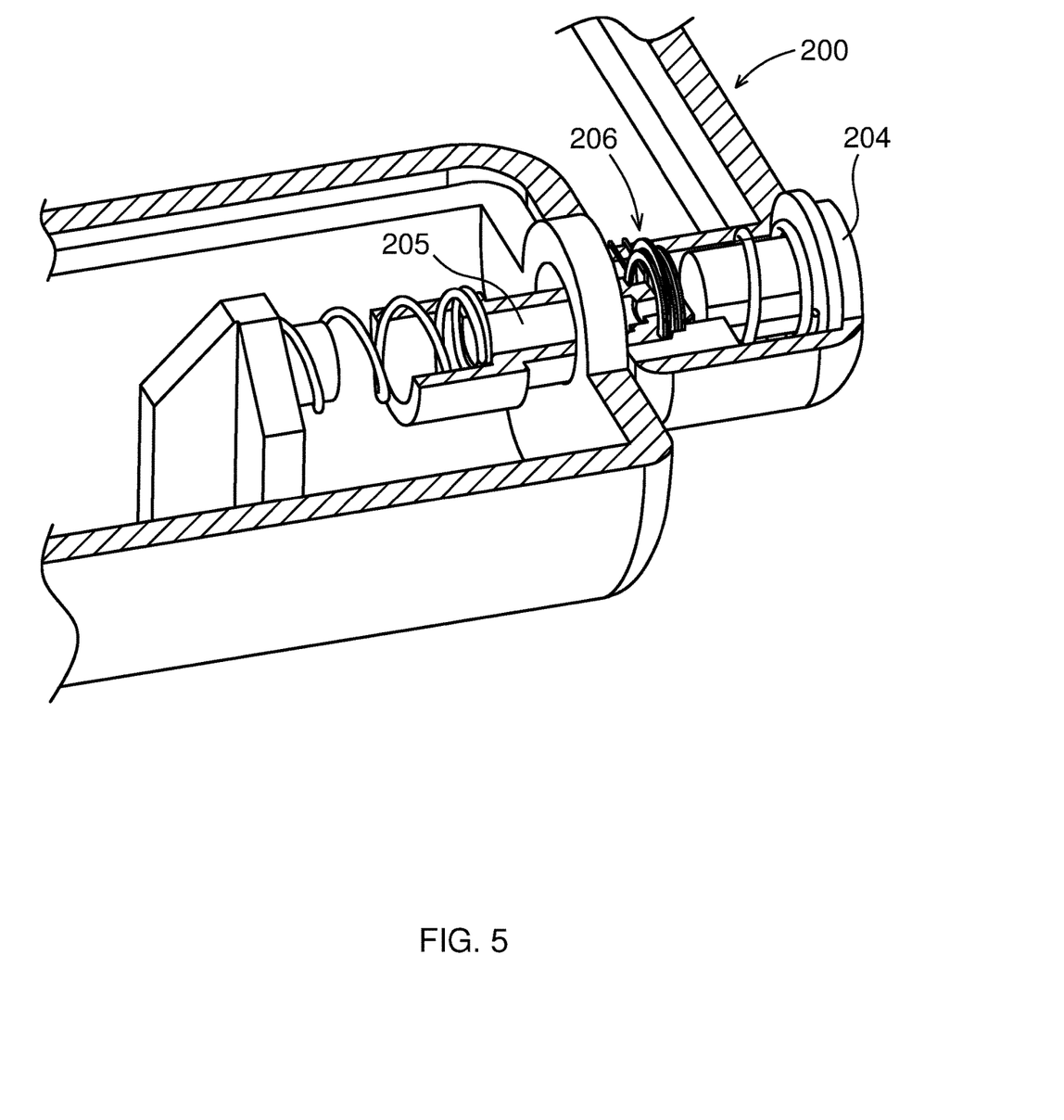
FIG. 5 is a partial perspective view of a powered quick disconnect for a toilet seat.

In accordance with the present disclosure, a design for a seat 200 that can be easily added/removed from a toilet, seat topper, seat lifter, etc. is provided. This allows for easier installation of a new seat 200 to accommodate upgraded seats and/or seat sensors. Referring to FIG. 5, a powered quick disconnect mechanism is shown. The seat 200 is removed by pressing in on the spring-loaded button 204. This moves the spring-loaded axle 205 out of the seat to allow the seat 200 to be removed. The electrical connector 206 automatically connects and disconnects with physical connection. The electrical connector 206 comprises a ring connector that maintains electrical connection throughout the seat's range of motion. This provides for electrical power and/or data connections to sensors in the seat.

A conventional toilet seat and lid are both connected to the toilet by a common hinge. The weight of the lid and seat, including a seated user, is supported by the body of the toilet. The toilet 100 of the present disclosure includes a seat 200 that is supported by load cells 203 that measure the weight on the seat 200. The load cells 203 may be supported by the body of the toilet or by an internal frame structure. The seat 200 is connected to the toilet 100 by a floating hinge 500 such that the hinge does not support the weight of the lowered seat.

Figure 6A:
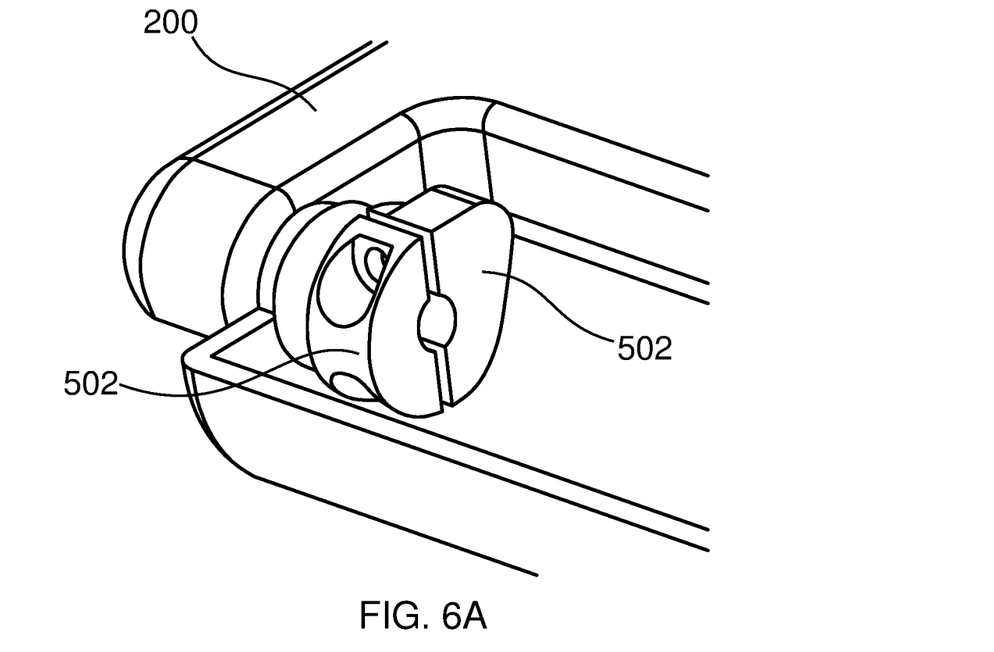
FIG. 6A is a partial perspective view of a floating hinge for a toilet seat according to the present disclosure.
Figure 6B:
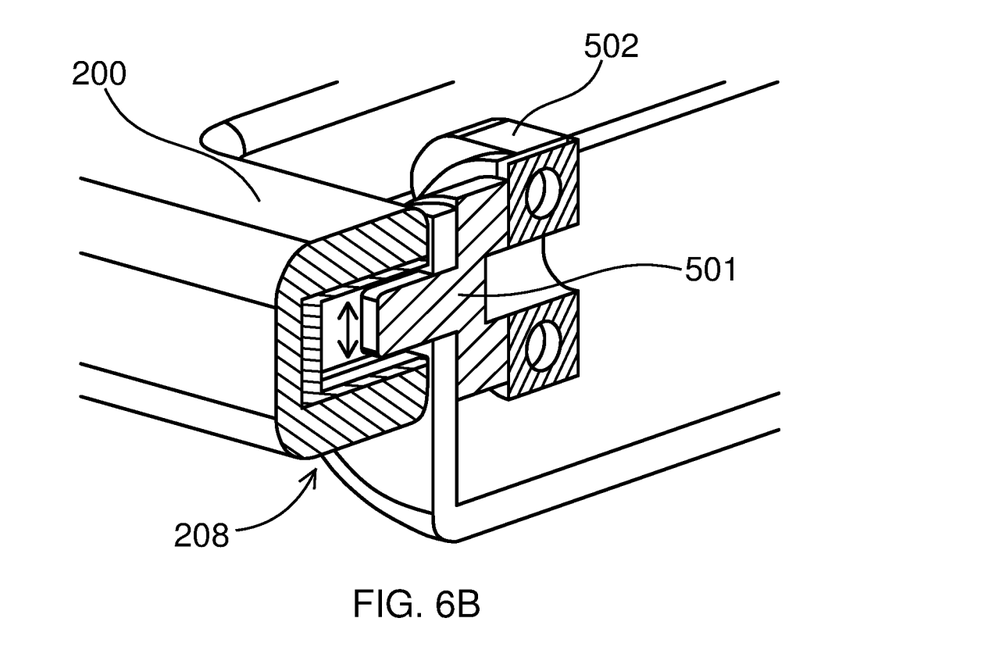
FIG. 6B is a partial perspective cross-sectional view of the floating hinge of FIG. 6A.

Referring to FIGS. 6A and 6B, an exemplary embodiment of a floating hinge 500 for a toilet seat 200 is shown. In this embodiment, the hinge axle 501 is fixedly attached to the hinge base 502 (i.e., the part of hinge attached to the toilet frame) and extending into, but is not physically connected to, the seat housing 208. As illustrated in FIG. 6B, the hinge axle 501 and seat housing 208 are designed to allow the seat to move vertically relative to the hinge axle 501. In another exemplary embodiment, the hinge design may be reversed such that the axle is fixedly attached to the seat and floats relative to the hinge base, which is fixedly attached to the toilet.

Figure 7A:
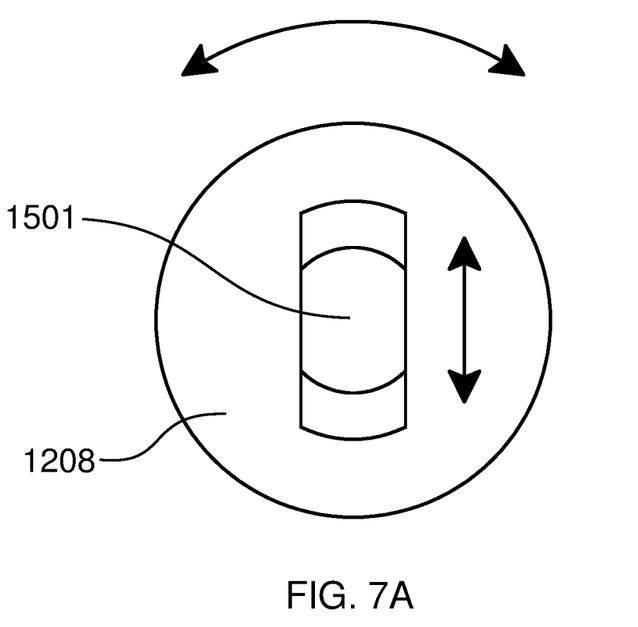
FIG. 7A is a cross-sectional end view of the axle housing of the floating hinge of FIG. 6A.
Figure 7B:
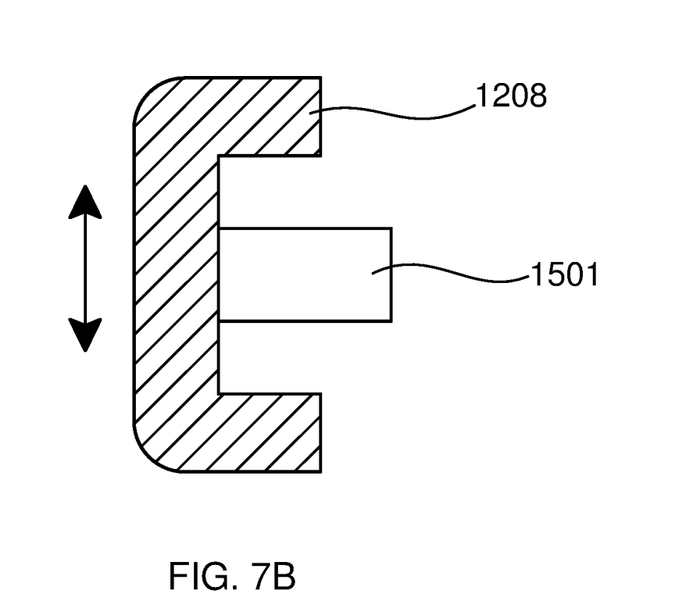
FIG. 7B is side cross-sectional view of the axle housing of FIG. 7A.

Referring to FIGS. 7A and 7B, examples of floating hinge connections are shown. FIG. 7A illustrates how axle 1501 and housing 1208 are able to move vertically, but not horizontally, relative to each other. The seat (not shown) may be rotatably attached to either housing 1208 or axle 1501. FIG. 7B is a cross-sectional view of the embodiment of FIG. 7A further illustrating the ability of the axle 1501 and the housing 1208 to move vertically, but not horizontally, relative to each other.

Figure 8A:
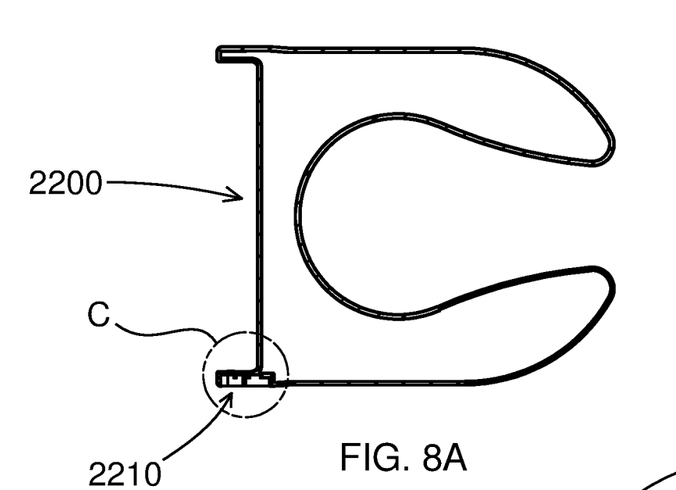
FIG. 8A is a top view of a second exemplary embodiment of a toilet seat with a floating hinge according to the present disclosure.
Figure 8B:
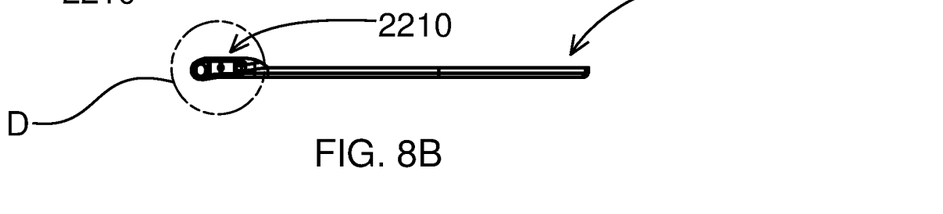
FIG. 8B is a side view of the toilet seat of FIG. 8A.
Figure 8C:
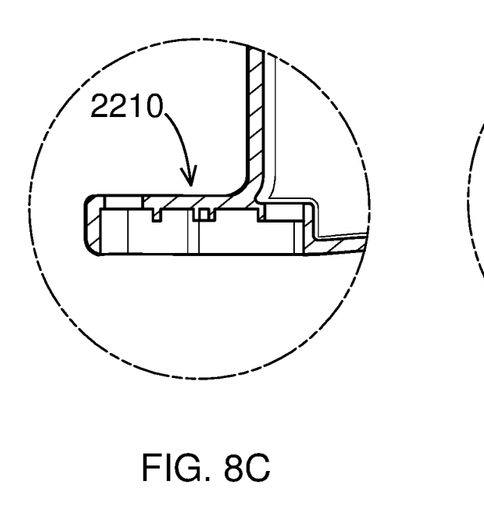
FIG. 8C is a cross-sectional view of the hinge of the toilet seat of FIG. 8A taken within Line C.
Figure 8D:
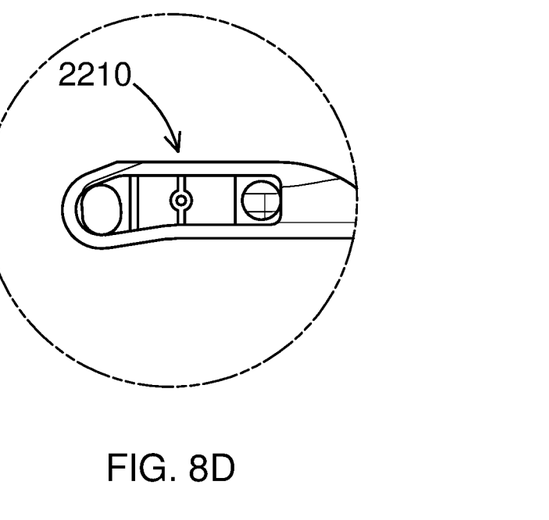
FIG. 8D is a cross-sectional view of the hinge of the toilet seat of FIG. 8A taken within Line D in FIG. 8B.

Referring to FIGS. 8A-D, another exemplary embodiment of a toilet seat 2200 with a floating hinge 2210 is shown. FIG. 8D shows the interior of hinge 2210. Some portions of the floating hinge 2210 may be integral to the seat or may be attached to the toilet seat 2200 with connectors (e.g., screws or bolts).

Figure 9A:
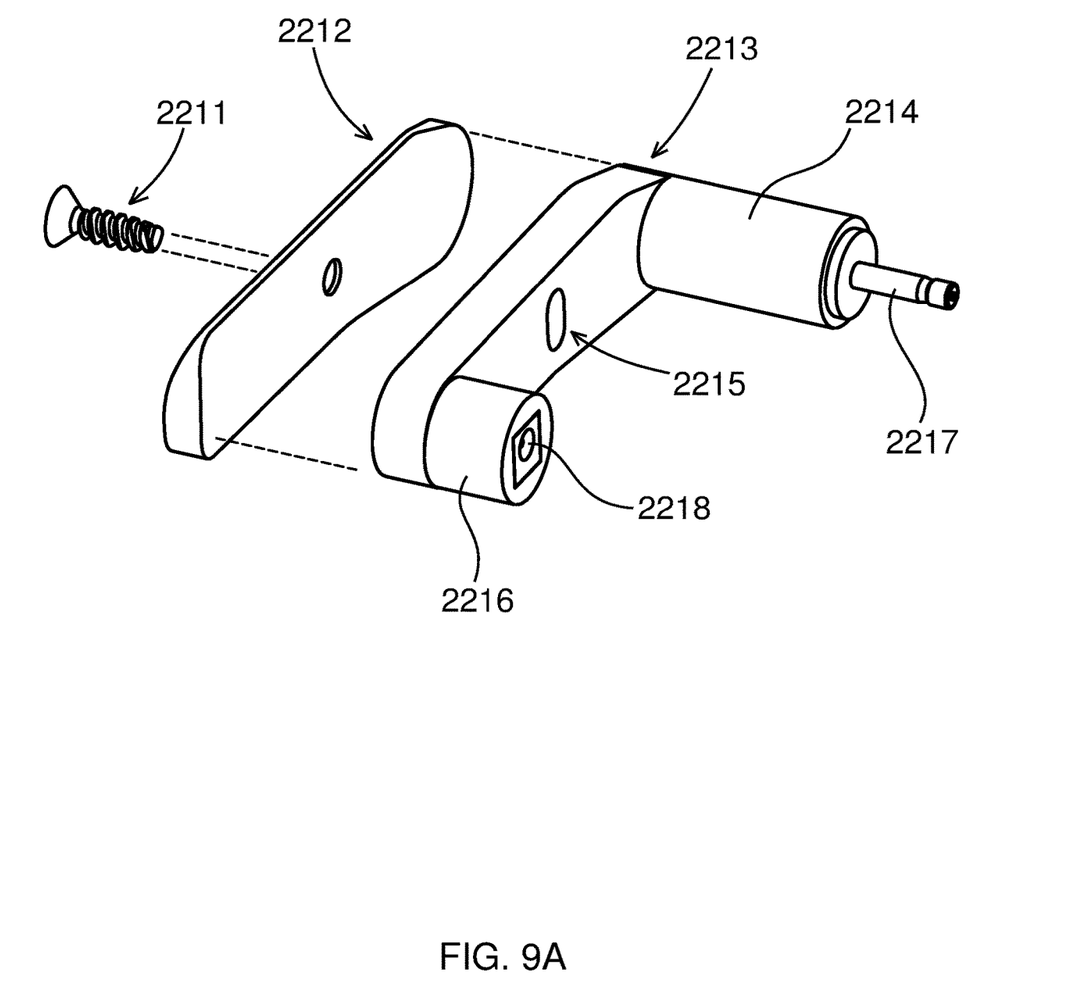
FIG. 9A is a first exploded perspective view of the hinge of the toilet seat of FIG. 8A.
Figure 9B:
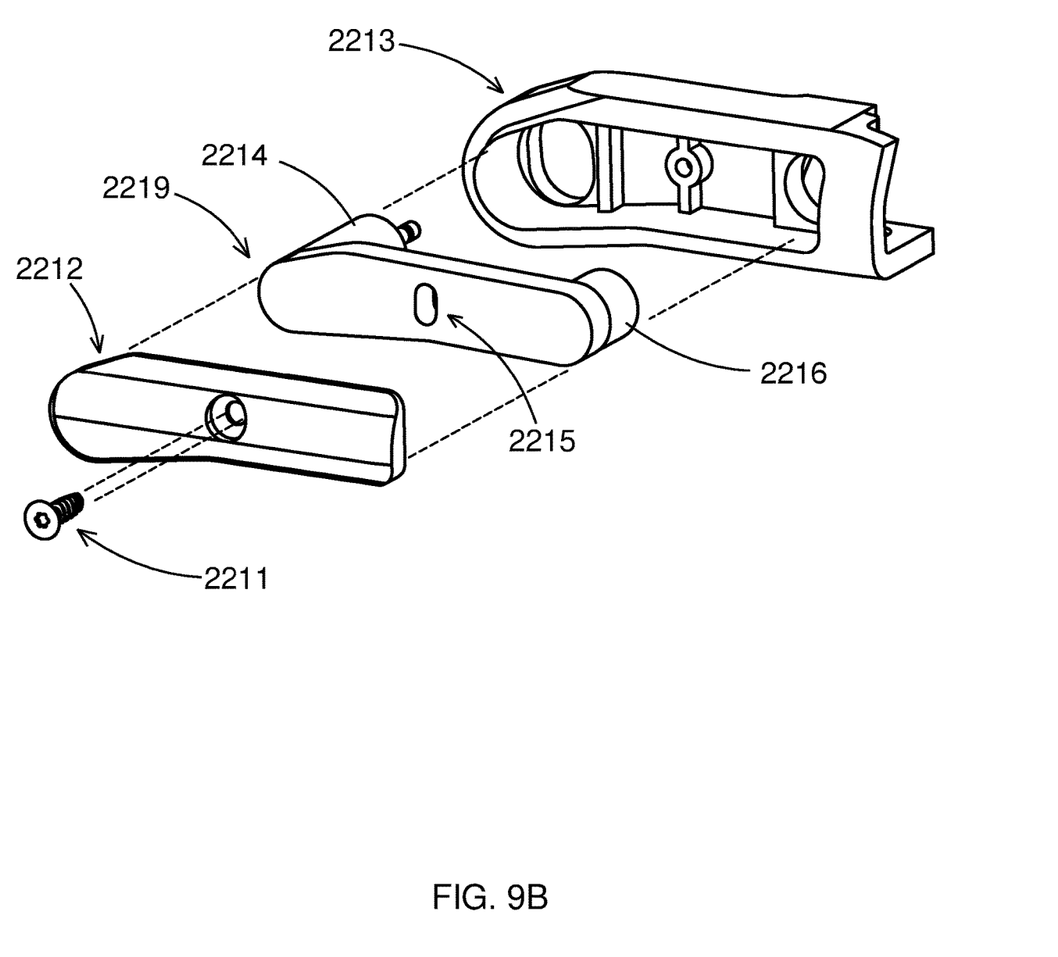
FIG. 9B is a second exploded perspective view of the hinge of the toilet seat of FIG. 8A.

Referring to FIGS. 9A-B, show the components of an exemplary floating hinge 2210. FIG. 9A shows one side of the hinge 2210 assembly. FIG. 9B shows it from the opposite side. In various exemplary embodiments, the hinge 2210 comprises a floating hinge case 2213, pivot bar 2219, and floating hinge cover 2212 connected by screw 2211. Screw 2211 connects the cover 2212 to the case 2213 enclosing the pivot bar 2219. In some embodiments, the screw 2211 also connects the hinge 2210 to the seat 2200.

In various exemplary embodiments, pivoting bar 2219 comprises seat axle 2214, screw slot 2215, pivot axle 2216, and electrical connectors 2217 and 2218. Seat axle 2214 is adapted to connect to the toilet and provides a point around which the seat 2200 is raised and lowered. The pivot axle 2216 rotatably connects the pivot bar 2219 to the hinge case 2213. As will be described in more detail below, the screw slot 2215 allows the pivot bar 2219 to pivot around the pivot axle 2216 without interacting with screw 2211.

In various exemplary embodiments, connectors 2217 and 2218 are included to provide a supply of electrical power to components within the seat, such as load cells, health and wellness sensors, processors, controllers, and wireless communications among others. Connectors 2217 and 2218 may also provide data connections to similar components elsewhere in the system. In preferred embodiments, the electrical wiring connecting connectors 2217 and 2218 are molded into the pivot bar 2219.

Figure 10A:
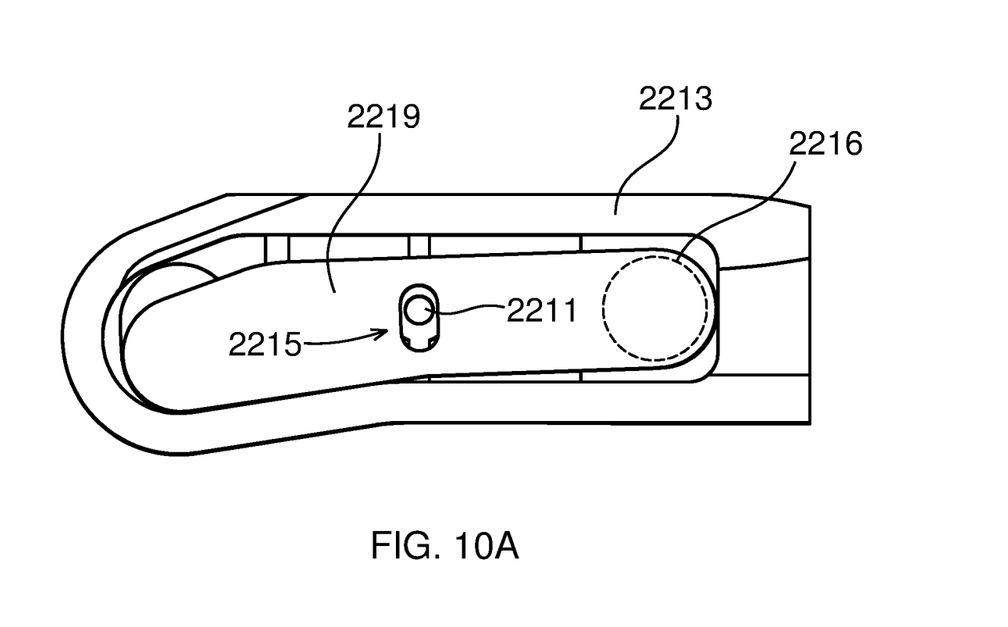
FIG. 10A is a side view of the internal parts of the hinge of FIG. 8A in a first position.
Figure 10B:
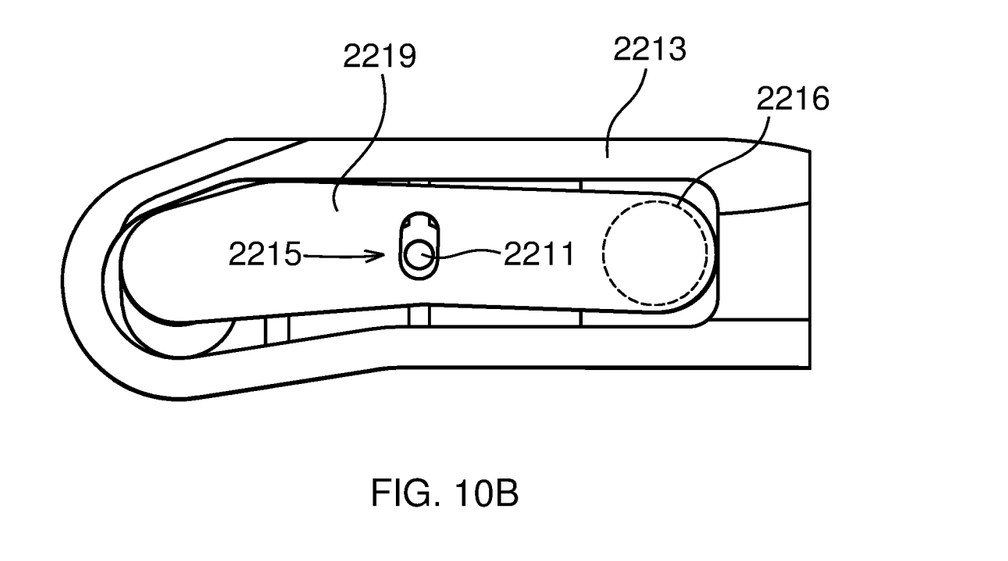
FIG. 10B is a side view of the internal parts of the hinge of FIG. 8A in a second position.

Referring to FIGS. 10A-B, illustrate the range of motion through which the floating hinge 2210 is able to float. Pivot bar 2219 rotates around the axis of pivot axle 2216 within hinge casing 2213. Screw slot 2215 is adapted to allow this without interference from screw 2211. Seat axle 2214 is able to move up and down relative to the hinge casing 2213 and vice versa. When a user sits on the toilet seat, the weight of the user may cause the seat and hinge casing 2213, which is fixed to the seat, to lower slightly causing pivot axle 2216 to lower. Seat axle 2214 does not move with the seat hinge casing 2213 because it is fixed relative to the toilet body and not to the seat. Because of the movement of pivot axle 2216, pivot bar 2219 moves relative to hinge casing 2213 such that seat axle 2214 moves upwardly and does not transfer the weight of the user from the seat and hinge casing 2213 to the toilet frame.

In various exemplary embodiments, the toilet seat lid comprises one or more health and wellness sensors that are adapted to interact with a seated user. The sensors may interact with the user's back while using the toilet or may be collecting data with the lid closed. The interior of the bowl may be illuminated with visual, infrared, near infrared, ultraviolet, or other wavelengths by light sources.

In various exemplary embodiments, the lid includes a seal that forms an airtight seal creating an airtight chamber including the bowl. In such embodiments, the toilet may include sensors for testing the air in the chamber and/or passages for drawing air out of the chamber for testing elsewhere in the system. Such sensors or tests may include electrocardiography, CCD, MOS/CMOS, spectrometers, chromatographs, FET, nano-FET, MOSFET, mass spectrometers, electrodes, microphones, load cells, pressure gauges, PPG, thermometers (including IR sensors and thermocouples), rheometers, durometers, pH detectors, and gas detectors.

In various exemplary embodiments, urine and feces are separated into different collection basins for independent weighing and/or other analysis. In various exemplary embodiments, cameras estimate the volume of the fecal matter and use the estimated volume to estimate density.

In various exemplary embodiments, the toilet is capable of determining the total weight of excreta and the separate weights of solids and liquids. For example, weight may be measured after completion of an excreta event. Liquids may be allowed to exit the bowl and a new weight measurement taken of the remaining solids. The difference in weight provides the weight of liquid excreta. Alternatively, the urine may be drained off at a known flow rate or through a flow meter to measure urine volume leaving only solids to be weighed.

In accordance with the present disclosure, a smart toilet that includes mechanical, hydraulic, power, and data connections to accommodate a combination of health measuring tools is provided. An electrical connection to provide power to the health measuring sensors is also provided.

In various exemplary embodiments, the smart toilet includes at least one sensor that analyzes imaging data. A processor analyzes the data to attempt to compare the user to known users for identification purposes. If a known user is identified, the position of the bowl and/or seat is automatically adjusted to the preferred position of the user. If the user is unknown or does not have a record preferred position, the processor analyzes the physical characteristics of the user (e.g., height, waist height, length of upper and lower legs) and adjusts the position of the bowl and/or seat accordingly. In some embodiments, facial recognition is used to identify users.

In various preferred embodiments, the system may identify a user based on their face, hand, or foot. In various preferred embodiments, the sensor may include a CCD (charge-coupled device) or MOS (metal oxide semiconductor), including CMOS (complementary metal oxide semiconductor). The sensor can be used, with proper calibration such as taking the data at a known distance, to measure the length of major bones. This data can then be used to customize the toiler position for an unknown user.

In various exemplary embodiments, the toilet system includes sensors for measuring the user's weight. This includes separate sensors for determining user weight on the seat and user weight on the user's feet. The user's weight that is supported by their feet is preferably measured using a platform adjacent to the toilet on which the user's feet are placed while sitting and while being lowered or raised from the toilet.

In the preferred embodiments, the toilet also includes health assessment devices supported by the frame. Examples of such devices include imaging sensors, flow spectrometers, volume measurement devices, body weight sensors, and gas analyzers. Toilets with such devices are described in the patents and published applications cited in the Background section above.

In various exemplary embodiments, the toilet includes at least one sensor receiving data from the load cells and/or health and wellness sensors. The processor is adapted to receive, process, and transmit data. The data may be transmitted to a remote data storage facility (e.g., cloud servers) and/or to the user's device (e.g., phone or computer).

All patents, published patent applications, and other publications referred to herein are incorporated herein by reference. The invention has been described with reference to various specific and preferred embodiments and techniques. Nevertheless, it is understood that many variations and modifications may be made while remaining within the spirit and scope of the invention.

What is claimed is:
1. An analytical toilet comprising:
a frame supporting a bowl for receiving excreta;
a floating seat for a user to sit above the bowl;
one or more seat load cells for measuring weight on the floating seat; and
a floating hinge connecting the floating seat to the frame;

wherein the floating hinge comprises a pivot bar rotatably connected to the floating seat at a first end and rotatably attached to the frame at a second end;

whereby the pivot bar pivots up or down at the first end as weight is added or removed from the floating seat.

2. The analytical toilet of claim 1 wherein the pivot bar is located in a hinge case.

3. The analytical toilet of claim 1 wherein the floating hinge further comprises an electrical connection between the floating seat and the toilet.

4. The analytical toilet of claim 1 further comprising a processor for receiving and transmitting data from the one or more seat load cells.

5. The analytical toilet of claim 1 further comprising a foot scale positioned in front of the toilet for measuring user weight.

6. The analytical toilet of claim 5 further comprising one or more foot scale load cells supporting the foot scale for measuring weight on the foot scale.

7. The analytical toilet of claim 6 further comprising a processor for receiving and transmitting data from the one or more foot scale load cells.

8. The analytical toilet of claim 1 further comprising further comprising at least one health and wellness sensor for determining at least one property of excreta.

9. The analytical toilet of claim 8 wherein the at least one property comprises one or more of volume, flow rate, color, weight, density, content, temperature, clarity, pH, settled gradient, and flow geometry of urine.

10. The analytical toilet of claim 8 wherein the at least one property comprises one or more of weight, color, consistency, volume, density, content, temperature, pH, size and shape, excretion profile, sounds, and gas or fumes of feces.

11. The analytical toilet of claim 8 wherein the at least one health and wellness sensor comprises one or more of electrocardiography, CCD, MOS, CMOS, spectrometers, chromatographs, FET, nano-FET, MOSFET, mass spectrometers, electrodes, microphones, load cells, pressure gauges, PPG, thermometers, rheometers, durometers, pH detectors, and gas detectors.

12. The analytical toilet of claim 8 further comprising a processor for receiving and transmitting data from the at least one health and wellness sensor.

13. The analytical toilet of claim 1 further comprising at least one health and wellness sensor for detecting health and wellness data about the user.

14. The analytical toilet of claim 13 wherein the at least one health and wellness sensor comprises one or more of electrocardiography, CCD, MOS, CMOS, spectrometers, chromatographs, FET, nano-FET, MOSFET, mass spectrometers, electrodes, microphones, load cells, pressure gauges, PPG, thermometers, rheometers, durometers, pH detectors, and scent detectors.

15. The analytical toilet of claim 13 wherein the at least one health and wellness sensor is located in at least one of the floating seat, a toilet lid, and a foot platform.

16. The analytical toilet of claim 13 further comprising a processor for receiving and transmitting data from the at least one health and wellness sensor.

* * * * *